(12) United States Patent
De Haan

(10) Patent No.: US 9,842,392 B2
(45) Date of Patent: Dec. 12, 2017

(54) DEVICE, SYSTEM AND METHOD FOR SKIN DETECTION

(71) Applicant: KONINKLIJKE PHILIPS N.V., Eindhoven (NL)

(72) Inventor: Gerard De Haan, Helmond (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 106 days.

(21) Appl. No.: 14/956,429

(22) Filed: Dec. 2, 2015

(65) Prior Publication Data

US 2016/0171684 A1 Jun. 16, 2016

(30) Foreign Application Priority Data

Dec. 15, 2014 (EP) .................................. 14197951

(51) Int. Cl.
| | |
|---|---|
| G06K 9/00 | (2006.01) |
| G06T 7/00 | (2017.01) |
| G06K 9/62 | (2006.01) |
| G06K 9/46 | (2006.01) |
| G06T 7/13 | (2017.01) |
| G06T 7/246 | (2017.01) |
| G06T 7/90 | (2017.01) |
| A61B 5/024 | (2006.01) |
| G06K 9/52 | (2006.01) |
| A61B 5/1455 | (2006.01) |
| A61B 5/00 | (2006.01) |

(52) U.S. Cl.
CPC ........ *G06T 7/0012* (2013.01); *G06K 9/00496* (2013.01); *G06K 9/4604* (2013.01); *G06K 9/4652* (2013.01); *G06K 9/6218* (2013.01); *G06K 9/6224* (2013.01); *G06T 7/13* (2017.01); *G06T 7/246* (2017.01); *G06T 7/90* (2017.01); *A61B 5/02416* (2013.01); *A61B 5/14551* (2013.01); *A61B 5/4887* (2013.01); *G06K 9/522* (2013.01)

(58) Field of Classification Search
None
See application file for complete search history.

(56) References Cited

U.S. PATENT DOCUMENTS

| | | | | |
|---|---|---|---|---|
| 6,185,314 B1 * | 2/2001 | Crabtree | ............... | G01S 3/7865 |
| | | | | 348/169 |
| 6,295,367 B1 * | 9/2001 | Crabtree | ............... | G01S 3/7865 |
| | | | | 382/103 |
| 6,611,628 B1 * | 8/2003 | Sekiguchi | ........... | G06F 17/3025 |
| | | | | 375/E7.001 |

(Continued)

OTHER PUBLICATIONS

Ron Van Luijtelaar, et al., "Automatic RoI Detection for Camera-Based Pulse-Rate Measurement", ACCV Workshop, Nov. 2, 2014.

(Continued)

*Primary Examiner* — Shervin Nakhjavan

(57) ABSTRACT

An input unit (20) obtains a sequence of image frames over time. A segmentation unit (22) segments image frames of the sequence of image frames. A tracking unit (24) tracks segments of the segmented image frame over time in the sequence of image frames. A clustering unit (26) clusters the tracked segments to obtain clusters representing skin of a subject by use of one or more image features of the tracked segments.

17 Claims, 11 Drawing Sheets

(56) References Cited

U.S. PATENT DOCUMENTS

| | | | | |
|---|---|---|---|---|
| 7,523,109 | B2* | 4/2009 | Weare | G06Q 10/10 |
| 2009/0141124 | A1* | 6/2009 | Liu | A61B 5/01 348/65 |
| 2009/0324008 | A1* | 12/2009 | Kongqiao | G06F 3/017 382/103 |
| 2010/0027845 | A1* | 2/2010 | Kim | G06K 9/6296 382/107 |
| 2011/0251493 | A1 | 10/2011 | Poh et al. | |
| 2011/0311143 | A1* | 12/2011 | Cennini | G06K 9/00255 382/191 |
| 2012/0194561 | A1* | 8/2012 | Grossinger | G06F 3/005 345/661 |
| 2013/0148898 | A1 | 6/2013 | Mitura et al. | |
| 2014/0334668 | A1* | 11/2014 | Saund | G06T 7/20 382/103 |
| 2015/0366456 | A1* | 12/2015 | Takamori | A61B 5/6898 600/480 |
| 2016/0117813 | A1* | 4/2016 | Gross | H04W 80/04 600/474 |
| 2016/0196657 | A1* | 7/2016 | Kantor | G06T 7/0057 382/154 |

OTHER PUBLICATIONS

Heo, et al., "Human Segmentation Algorithm for Real-time Video-call applications", 2013.

Gonzalez, et al., "A Generative Model for Concurrent Image Retrieval and ROI Segmentation", IEEE Transactions on Multimedia; Jan. 2014, vol. 16 Issue 1.

Gibert, et al., "Face Detection Method based on Photoplethysmography", Aug. 2013.

Verkruysse et al., "Remote plethysmographic imaging using ambient light", Optics Express, 16(26), Dec. 22, 2008, pp. 21434-21445.

Wieringa, et al., "Contactless Multiple Wavelength Photoplethysmographic Imaging: A First Step Toward "SpO2 Camera" Technology", Ann. Biomed. Eng. 33, 1034-1041 (2005).

C. Harris and M. Stephens, "A combined corner and edge detector", Proceedings of the 4th Alvey Vision Conference, 1988, pp. 147-151.

Delaunay, Boris: "Sur la sphère vide. A la mémoire de Georges Voronoï", Bulletin de l'Académie des Sciences de l'URSS, Classe des sciences mathématiques et naturelles, No. 6: 793-800, 1934.

* cited by examiner

DEVICE, SYSTEM AND METHOD FOR SKIN DETECTION

CROSS-REFERENCE TO PRIOR APPLICATION

This application claims the benefit of European Patent Application No. 14197951.8 filed Dec. 15, 2014. The application is hereby incorporated by reference herein.

FIELD OF THE INVENTION

The present invention relates to a device, system and method for skin detection.

BACKGROUND OF THE INVENTION

Vital signs of a person, for example the heart rate (HR), the respiration rate (RR) or the arterial blood oxygen saturation (SpO2), serve as indicators of the current health state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen saturation can be determined.

Recently, non-contact, remote PPG (rPPG) devices (also called camera rPPG devices) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. This technology particularly has distinct advantages for patients with extreme skin sensitivity requiring vital signs monitoring such as Neonatal Intensive Care Unit (NICU) patients with extremely fragile skin or premature babies.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue color channels.

Wieringa, et al., "Contactless Multiple Wavelength Photoplethysmographic Imaging: A First Step Toward "SpO2 Camera" Technology", Ann. Biomed. Eng. 33, 1034-1041 (2005), discloses a remote PPG system for contactless imaging of arterial oxygen saturation in tissue based upon the measurement of plethysmographic signals at different wavelengths. The system comprises a monochrome CMOS-camera and a light source with LEDs of three different wavelengths. The camera sequentially acquires three movies of the subject at the three different wavelengths. The pulse rate can be determined from a movie at a single wavelength, whereas at least two movies at different wavelengths are required for determining the oxygen saturation. The measurements are performed in a darkroom, using only one wavelength at a time.

Apart from the advantage of being fully contactless, cameras (generally called imaging devices) provide 2D information, which allows for a multi-spot and large area measurement, and often contains additional context information. Unlike with contact sensors, which rely on the correct placement on a specific measurement point/area, the regions used to measure pulse signals using rPPG technology are determined from the actual image. Therefore, accurate detection of skin areas, reliable under any illumination conditions becomes a crucial part in the processing chain of a camera-based rPPG device and method used for camera-based vital signs monitoring.

Currently, there are two main approaches known for reliable detection and tracking of a skin areas.

One approach is based on skin color (RGB-based) detection and segmentation. Methods according to this approach are fast in both detection and tracking of areas with skin color. However, they are not robust to changes of ambient light color, which will change the color of light reflected from a skin area, and are not able to detect skin areas under low illumination conditions or in darkness. Moreover, such methods cannot always differentiate a skin from other objects with the same color.

Another approach is based on extracted PPG signals (PPG-based). Methods according to this approach are more robust in differentiating real skin areas and areas of other object of the same skin color. This approach can be used also to segment the skin areas, which have stronger PPG signal (the most periodic signal). However, the reliability of the approach depends on the robustness of PPG signal extractions, thus it is impacted by motion of a subject and the blood perfusion level. Therefore, if a pulse signal is not periodic or is weak, a camera-based system will have difficulties to detect the segment the skin areas. Moreover, the approach is also computationally expensive.

It should be noted that the detection of skin area is not only of interest in the field of vital signs detection based on the rPPG technology, but also in other technical fields, e.g. in remote gaming applications using camera technology to recognize gestures of the player, face detection, security (robust detection of a person using surveillance cameras and detection of a person wearing a mask or distinguishing real faces from a realistic mask in a camera registration), etc.

A problem with surveillance camera images is that it is difficult to distinguish between a face and a mask or a picture of a face. A problem with camera-based vital signs monitoring is that the vital signs can only be extracted from living tissue, usually some skin-area, but currently this area is most often manually selected from the video and consequently tracked, or one has to rely on a face detector that typically fails on side views of a face, and certainly does not give anything useful for non-facial skin in the video. Hence, there is still a need for ways to reliably, accurately and quickly find every useful skin surface.

SUMMARY OF THE INVENTION

It is an object of the present invention to provide a device and a corresponding method as well as a system which allow a reliable, accurate and fast detection of skin.

In a first aspect of the present invention a device for skin detection is presented comprising
   an input unit for obtaining a sequence of image frames acquired over time,
   a segmentation unit for segmenting an image frame of said sequence of image frames,
   a tracking unit for tracking segments of the segmented image frame over time in said sequence of image frames,
   a clustering unit for clustering the tracked segments to obtain clusters representing skin of a subject by use of one or more image features of said tracked segments.

In a further aspect of the present invention a corresponding method for skin detection is presented.

In a still further aspect of the present invention a system for skin detection is presented comprising
   an imaging unit for acquiring a sequence of image frames over time and
   a device as disclosed herein for skin detection based on the acquired sequence of image frames.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed methods, processor, computer program and medium have similar and/or identical preferred embodiments as the claimed system and as defined in the dependent claims.

The present invention solves the problems and disadvantages of the known methods and devices using a three step approach. First, in the analysis window (time-interval) an image (mostly the first of the window) is segmented. Next, individual segments are tracked over time (resulting in tracked segments over time which each may also be considered as a volume). Said tracking is performed by use of one or more features, including features describing the temporal domain, which e.g. have been extracted from the tracked segments (volumes). Finally, a clustering is performed of said tracked segments based on said features identifying one or more clusters that contain living tissue, i.e. skin area, and possibly one or more clusters that do not contain any living tissue. This allows a reliable, accurate and fast detection of skin in a sequence of image frames as typically acquired by a video camera.

In an embodiment said segmentation unit is configured to over-segment the image frame that is used for segmentation. Generally, an assumption is made with respect to the (minimum) size of the living tissue (skin area) that shall be detected in the image frames. The proposed "over-segmentation" aims at finding initial segments that are smaller than this minimum size. Often, in segmentation, there is some parameter to be chosen that determines the number of segments that are found. For example in a feature point detector it is possible to set a minimum quality of a feature point which affects the number of features that can be found. Preferably, said segmentation unit is configured to over-segment the image frame that is used for segmentation based on color, position and/or texture properties.

The aim of the over-segmentation is to have at least a number of segments that only contain living tissue and no background as could occur with larger segments resulting from the triangulation. At the same time, the segments should be large enough to allow for extraction of a pulse-signal with sufficient SNR to be used as a feature in clustering the segments belonging to tissue of the same living being.

In another embodiment said clustering unit is configured to use temporal color variations of the tracked segments as feature for clustering the tracked segments. For instance, said clustering unit may be configured to perform a Fourier transformation of the spatially combined color value of at least part of the pixels in a tracked segment and to cluster two tracked segments into a single cluster if their amplitude peak frequency has substantially the same value and phase. Hence, to know if two tracked segments belong to the same cluster (i.e. to living being) the frequency and the phase of their temporal color variations may be compared. This provides for a rather simple but efficient way of clustering.

In another embodiment said clustering unit is configured to compute the inner product between normalized time signals of different tracked segments and to cluster said tracked segments into a single cluster if said inner product exceeds a predetermined threshold. Said time signals are preferably color signals in a time window, which may be normalized by their mean in that window. The higher the value of the inner product is, the more similar the tracked segments are. This provides for another rather simple but effective way of clustering.

In still another embodiment said clustering unit is configured to use the hue of pixels of the tracked segments as feature for clustering the tracked segments, which provides for still another rather simple but effective way of clustering. It would also be possible to require that "members" of a cluster are connected to other members. However, different skin parts may not necessarily have the same hue and also can be unconnected due to clothing etc. so that such features are preferably used in addition to other features for clustering.

Preferably, said segmentation unit, said tracking unit and said clustering unit are configured to repeatedly perform segmentation, tracking and clustering, wherein the sequence of acquired image frames used for subsequent repetitions overlap in time. Hence, successive (time) windows of image frames are preferably processed sequentially, which successive windows are partially overlapping.

The segmentation unit may be configured to perform a feature point detection, in particular a Harris corner detection, or a triangulation, in particular a Delaunay triangulation. A Harris corner detector is e.g. described in C. Harris and M. Stephens, "A combined corner and edge detector", Proceedings of the 4th Alvey Vision Conference, 1988, pp. 147-151. It considers the differential of a corner score with respect to direction directly, instead of using shifted patches. A Delaunay triangulation is e.g. described in Delaunay, Boris: "Sur la sphère vide. A la mémoire de Georges Voronoï", Bulletin de l'Académie des Sciences de l'URSS, Classe des sciences mathématiques et naturelles, No. 6: 793-800, 1934. A Delaunay triangulation for a set P of points in a plane is a triangulation DT(P) such that no point in P is inside the circumcircle of any triangle in DT(P). Delaunay triangulations maximize the minimum angle of all the angles of the triangles in the triangulation; they tend to avoid skinny triangles. These methods are advantageous (but not the only) options for performing the segmentation.

In still another embodiment said tracking unit is configured to track the segments of the segmented image frame using motion estimation. Other options may be the use of any tracking based on appearance, e.g. using face detection or object detection which allows tracking of an image part.

Still further, the device may further comprise a vital signs detector for detecting vital signs of a subject based on image information from detected skin areas within said sequence of image frames. Preferably, the rPPG technology is applied for obtaining the vital signs.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
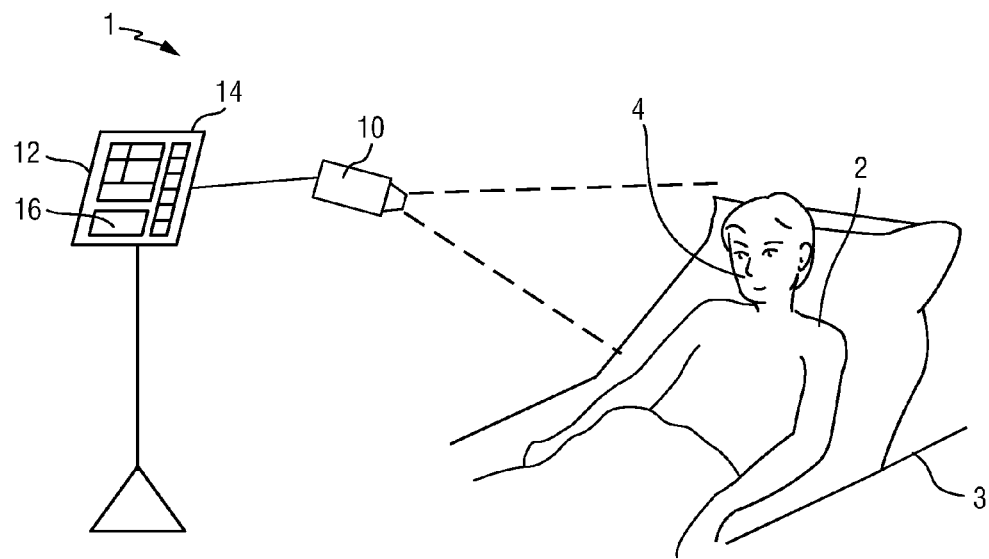
FIG. 1 shows a schematic diagram of an embodiment of a system according to the present invention.

FIG. 1 shows a schematic diagram of a first embodiment of a system 1 for skin detection according to the present invention. The system 1 comprises an imaging unit 10 for acquiring a sequence of image frames of a scene over time. The scene includes, in this example, a patient 2 lying in a bed 3, e.g. in a hospital room or other healthcare facility, but may also be the environment of a neonate or premature infant, e.g. lying in an incubator/warmer, or a person at home or in a different environment. The imaging unit 10 is particularly a camera (also referred to as detection unit or as camera-based or remote PPG sensor), which is configured to obtain images of the scene, preferably including skin areas 4 of the patient 2. In an application of the device for obtaining vital signs of the patient 2, the skin area 4 is preferably an area of the face, such as the cheeks or the forehead, but may also be another area of the body, such as the hands or the arms.

The image frames captured by the camera may particularly correspond to a video sequence captured by means of an analog or digital photosensor, e.g. in a (digital) camera. Such a camera usually includes a photosensor, such as a CMOS or CCD sensor, which may also operate in a specific spectral range (visible, IR) or provide information for different spectral ranges. The camera may provide an analog or digital signal. The image frames include a plurality of image pixels having associated pixel values. Particularly, the image frames include pixels representing light intensity values captured with different photosensitive elements of a photosensor. These photosensitive elements may be sensitive in a specific spectral range (i.e. representing a specific color). The image frames include at least some image pixels being representative of a skin portion of the person. Thereby, an image pixel may correspond to one photosensitive element of a photo-detector and its (analog or digital) output or may be determined based on a combination (e.g. through binning) of a plurality of the photosensitive elements.

The system 1 further comprises a device 12 according to the present invention for skin detection based on the acquired sequence of image frames. An embodiment of the device 12 will be explained in more detail below with reference to FIG. 2.

The system 1 may further comprise a controller 14 for controlling the other elements of the system, a user interface 16, such as a keyboard and/or a display, for entering commands for controlling the system 1 and/or outputting generated information, such as obtained vital signs. These elements 14 and 16 may be part of the device 12, as shown in FIG. 1, or may be separate elements.

Figure 2:
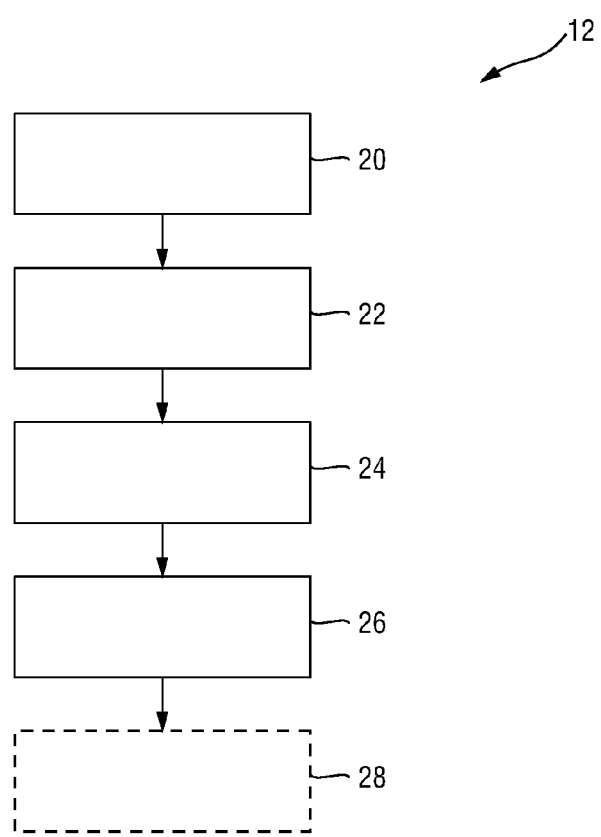
FIG. 2 shows a schematic diagram of an embodiment of a device according to the present invention.

A schematic diagram of an embodiment of a device 12 for skin detection according to the present invention is shown in FIG. 2. The device 12 comprises an input unit 20 for obtaining a sequence of image frames acquired over time, either directly from the imaging unit 10 or from a storage (not shown). The input unit 20 may be a data interface for wired or wireless reception of data, e.g. via a network or via a direct link.

The device 12 further comprises a segmentation unit 22 for segmenting an image frame of said sequence of image frames, a tracking unit 24 for tracking segments of the segmented image frame over time in said sequence of image frames and a clustering unit 26 for clustering the tracked segments to obtain clusters representing skin of a subject by use of one or more image features of said tracked segments. The function of these units 22, 24, 26 will be explained in more detail below.

The device 12 optionally further comprises a vital signs detector 28 for detecting vital signs of the subject 2 within the scene based on image information from detected skin areas within a sequence of images acquired by the imaging unit 10. The vital signs detector 28 preferably applies the remote PPG technique to obtain vital signs from said image information, e.g. heartbeat, SpO2, etc.

The different units of the device 12 may be configured as dedicated hardware elements, but may also be configured as processor or computer, which is programmed accordingly. The device 12 may be configured as integrated device including all these units, e.g. in a common housing (e.g. in the housing of the imaging unit 10) or as distributed device, i.e. implemented as separate elements and units. Preferably, the device 12 is configured as computer programmed with an appropriate for carrying out the functions of the units of the device 12.

Preferably, the segmentation unit 22 over-segments an image, i.e. segments the image frame into smaller segments as conventionally required or used for segmentation. Although the (over)-segmentation can use alternative features, in an embodiment a triangulation of the image based on Harris feature points is used, as this elegantly solves the segment-tracking over time with low computational effort. Corner detection, as used in a Harris detector, works on the principle that if a small window is placed over an image, if that window is placed on a corner then if it is moved in any direction there will be a large change in intensity. If the window is over a flat area of the image then there will be obviously be no intensity change when the window moves. If the window is over an edge there will only be an intensity change if the window moves in one direction. If the window is over a corner then there will be a change in all directions, and therefore it will be known that there must be a corner. A Harris corner detector measures the strength of detected corners, and only marks those above a given strength as actual corners.

Alternatively, a dense motion estimation could have been performed, assigning a motion vector to every pixel or region in the image, and use these motion vectors to track any (e.g. color) segmentation.

Further, it is even possible to consider every pixel a segment, provided the pixels have a low enough (quantization) noise-level. To achieve such good noise level, pixels may be grouped into blocks (fixed grid) as initial segmentation.

As a further alternative the image could be down-scaled to a lower spatial resolution such that the resulting low-resolution pixels have a good SNR due to the spatial averaging of the down-scaling filter.

Whatever the segmentation and tracking method used, different tracked segments are successively clustered based on minute temporal variations of the color that are characteristic for living tissue and caused by cardiac activity. Using the frequency and phase of these color variations, tissue from multiple subjects can be distinguished and disjunct tissue parts belonging to the same individual end up in the same cluster.

In the following a detailed embodiment of the proposed method shall be explained comprising three main stages: (1) region tracking (2) feature extraction and (3) region clustering. First, the first image in a predefined interval is divided in adjacent regions which are tracked during the remaining images in the interval. Second, discriminative information related to skin is extracted from these regions as a feature vector. Third, a clustering of regions is performed using the feature vector to determine the ROI.

As a tradeoff between estimation accuracy and computational complexity, the images in a predefined interval are segmented in adjacent regions. To obtain accurate pulse signals, the relocation of all points in the region is determined in order to compensate for movement artifacts; however this can prove to be a very time consuming task. As an alternative solution, the trajectory of solely boundary points can be tracked assuming that relocation of the interior points is similar. For this approach, points suitable for tracking are located in the initial image of the interval and their trajectories are estimated for the entire interval. Regions shaped as triangles are established using triangulation derived from these points.

Figure 3A:
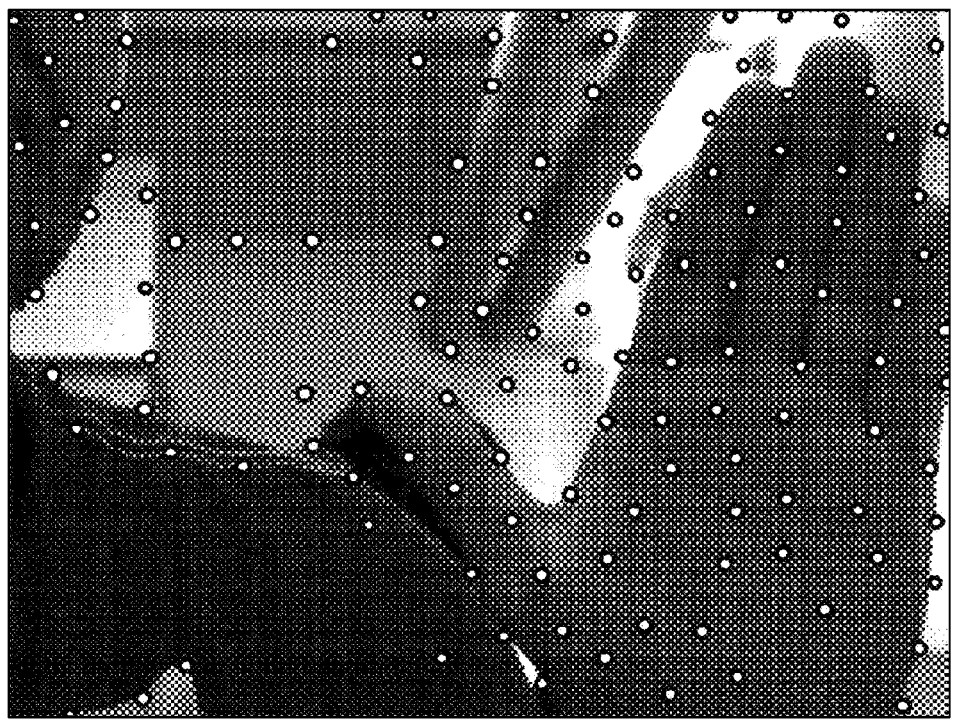
FIG. 3A shows an image frame illustrating triangulation as used in an embodiment of the present invention.

Suitable points for tracking are only located in areas of the image containing the complete motion information. This restriction is known as the aperture problem and can be resolved by selecting points where two edges intersect (corner points). In this embodiment, the corner detection method proposed by Harris & Stephens as e.g. described in the above cited document is implemented for the detection of trackable interest points. For each point $p=[x\ y]^T$ in the image, a corner response measure R is computed which is defined as:

$$R = Det(M) - k[Tr(M)]^2 \quad (1)$$

where k is a tunable sensitivity parameter and M is a 2×2 symmetric matrix given by:

$$M = \sum_{u,v \in N(x,y)} w(u,v) \begin{bmatrix} I_x^2 & I_x I_y \\ I_x I_y & I_y^2 \end{bmatrix} \quad (2)$$

where $I_x$ and $I_y$ denote the image derivatives in the horizontal and vertical direction within a neighborhood $N(x, y)$. The weighting function $w(u, v)$ is shaped as a circular Gaussian to smooth the corner response. By applying a threshold, the points with a corner response R greater than a certain value can be considered as corner points and are therefore suitable for tracking. In FIG. 3A, interest points suitable for tracking according the corner detection are shown for a video sequence containing a hand.

After detection the interest points in the initial frame of the interval, these points are tracked during the remaining images in the interval. To find the trajectory of a point $p=[x, y]^T$ the displacement vector $\Delta=[d_x, d_y]$ between consecutive images is obtained which minimizes the following equation:

$$e(d_x, d_y) = \sum_{u,v \in N(x,y)} [I(u,v) - J(u+d_x, v+d_y)]^2 \quad (3)$$

Under the assumption that the displacement of the image contents between the two images I and J is not too large and is approximately constant within a neighborhood $N(x, y)$, this optimization problem can be efficiently solved using e.g. a method as described in B. D. Lucas, "An Iterative Image Registration Technique with an Application to Stereo Vision", vol. 130, pp. 121-130, 1981. To accommodate for large displacement, an image pyramid implementation of the Lucas Kanade tracker described in J-Y Bouget, "Pyramidal implementation of the Affine Lucas Kanade feature tracker, Description of the algorithm", Intel Corporation, Microprocessor Research Labs may be used in this embodiment. In this approach, the displacement vector found on an upper pyramid level is propagated onto the lower levels and refined using the high frequency details.

There are two cases where an interest point might be considered as "lost". The first case is that the estimated position of an interest point falls outside the boundaries of the image and can be readily verified. The second case is when an interest point is disappearing due occlusion and may be declared "lost" if the optimal $\epsilon(\tilde{d}_x, \tilde{d}_y)$ exceeds a certain threshold. However, since the tracking is based on consecutive pairs of images, the displacement errors are inherently small and choosing a threshold is a challenging task. As occlusion areas cause unreliable displacement estimates, a symmetry check is included where the actual position $p_f = [x\ y]^T$ is compared with the estimated $\hat{p}_f = [\tilde{x}\ \tilde{y}]^T$ resulting from the 'backward' displacement estimate using $p_f = [x + \tilde{d}_x, y + \tilde{d}_x]^T$. In case the difference in these locations is larger than a certain value, currently set to 2 pixels, the interest point is considered "lost" and is not tracked further.

Figure 3B:
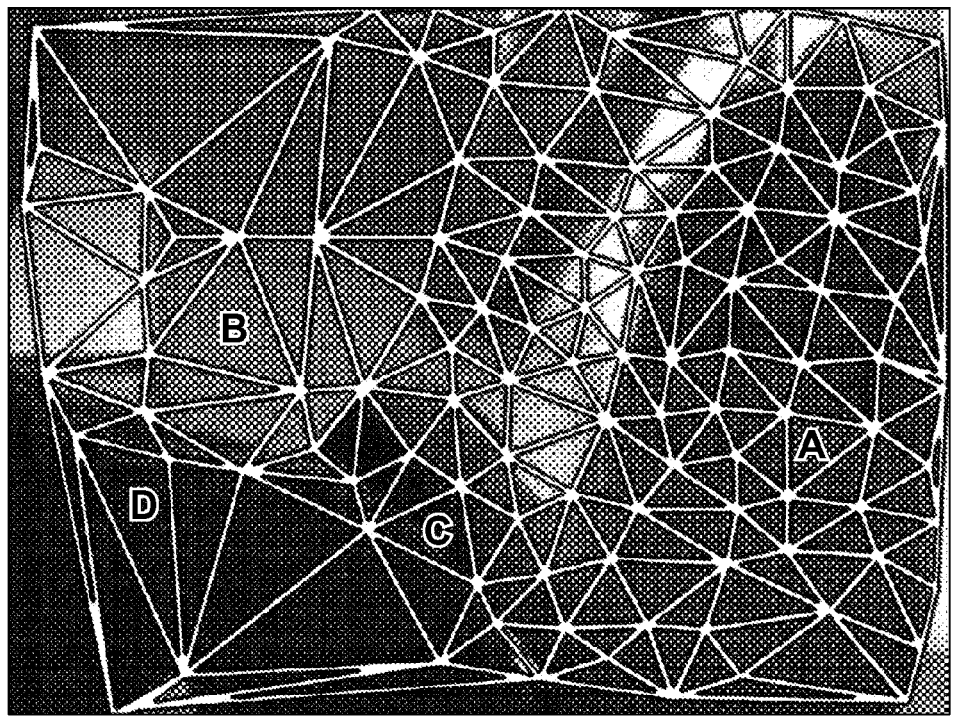
FIG. 3B shows an image frame illustrating triangulation as used in an embodiment of the present invention.

As discussed above, some interest points can disappear when moving outside the image or due to occlusion. Deriving triangles using the detected interest points and tracking these triangles is a valid option; however, in doing so there is a risk to have triangles discarded if one interest point disappears. The triangulation is therefore performed using interest points that are successfully tracked during the complete interval. In order to avoid triangles with a large ratio between the largest and shortest edge, i.e. skinny triangles, Delaunay triangulation is applied. This method attempts to maximize the minimum angle of all the angles of the triangles in the triangulation. FIG. 3B shows the resulting regions for the example sequence.

Following the region tracking, R, G and B traces are composed for each region by concatenating the average pixel values of every image in the interval. The pulse signal for all regions in the interval is computed using the method $X_s \min \alpha Y_s$ as described in G. de Haan and V. Jeanne, "Robust pulse-rate from chrominance-based rPPG", IEEE transactions on bio-medical engineering, no. c, pp. 1-9, June 2013. This chrominance-based method is using a combination of two orthogonal chrominance signals X=R−G and Y=0.5R−0.5G−B and is therefore capable of eliminating specular reflection changes due to movement assuming of a white light source. In order to enable correct functioning with colored light sources, skin-tone standardization is applied resulting in the following equation:

$$X_s = 3R_n + 2G_n$$

$$Y_s = 1.5R_n + G_n - 1.5B_n \quad (4)$$

where $R_n$, $G_n$ and $B_n$ are normalized color channels by dividing the samples by their mean over the interval to provide a pulse signal that is independent of the brightness of the light source. The difference between $X_s$ and $Y_x$ is considered as the pulse signal:

$$S = X_f - \alpha Y_f \quad (5)$$

with $$\alpha = \frac{\sigma(X_f)}{\sigma(Y_f)} \quad (6)$$

where $\sigma(X_f)$ and $\sigma(Y_f)$ are the standard deviations of $X_f$ and $Y_f$ which are the band-passed filtered versions of $X_s$ and $Y_s$. The normalized color traces $R_n$, $G_n$ and $B_n$ and resulting pulse signals are given in FIGS. 4 to 7 for regions indicated in FIG. 3B. After obtaining the set of temporal color traces $R_n$, $G_n$ and $B_n$ shown in FIGS. 4A, 5A, 6A, 7A, and pulse signal S shown in FIGS. 4B, 5B, 6B, 7B for each region in the interval, discriminant features for clustering are extracted. These features should summarize unique characteristics of skin regions. FIGS. 4C, 5C, 6C, 7C show normalized spectra of pulse signals V and normalized spectra W of auto-correlation of pulse signals.

Similar to the existing pixel based skin detection methods described above the fact that the color properties for skin regions within a given image are at close range is preferably used. A disadvantage of using the RGB color space representation is its sensitivity to illumination intensity changes. To enhance robustness towards changes in illumination and shadows, the color space can be transformed into a color space where the intensity is separated from the intrinsic information of color. Therefore, the Hue-Saturation-Value (HSV) color space is used in an embodiment where the value component which is related to the intensity is and the saturation are disregarded. The hue is computed using the following equation:

$$H = \begin{cases} 60 \times \left(\frac{G-B}{C} \mod 6\right), & \text{if } M = R \\ 60 \times \left(\frac{B-R}{C} + 2\right), & \text{if } M = G \\ 60 \times \left(\frac{R-G}{C} + 4\right), & \text{if } M = B \end{cases} \quad (7)$$

where the average pixel values $\{R, G, B\} \in [0, 1]$ and chroma C is defined as:

$$C = M - m \quad (8)$$

where $$M = \max(R, G, B)$$

$$m = \min(R, G, B) \quad (9)$$

Furthermore, similar skin regions corresponding to a particular body part are closely located in each instantaneous frame. The position of the geometric center P of each region is computed by averaging over the positions of the corner points belonging to the region:

$$P = \frac{1}{N} \sum_{n=0}^{N-1} P_n \quad (10)$$

To describe the periodicity of the pulse signal S, a spectral analysis may be performed. Therefore, the Discrete Fourier Transfer (DFT) may be used which transforms the time domain signal by correlating the signal with cosines and sines of different frequencies as follows:

$$\hat{S}[k] = \sum_{n=0}^{N-1} S[n] e^{-j 2\pi \frac{kn}{N}}, 0 \le k \le N - 1 \quad (11)$$

where N is the number of frames in the given interval. To retrieve an acceptable spectral resolution, the length of the interval is fixed at N=128 (6.4 sec) and the resulting spectrum is interpolated to obtain 512 FFT bins. FIGS. 4C, 5C, 6C, 7C show examples of $S_i$ where $i \in \{A, B, C, D\}$ in the spectral domain for the different regions in FIG. 3B. The spectrum of $S_A$ consists of a dominant frequency whereas the distribution of frequencies for $S_B$ is significantly wider. In practice, movement and imperfections of the camera introduce several noise components into the pulse signal. To reduce the influence of noise on the frequency spectrum, the DFT of the auto-correlation is computed since this will suppressed the noise while retaining the periodicity of the pulse signal.

FIGS. 4C, 5C, 6C, 7C show examples of the auto-convolution of $S_i$ where $i \in \{A, B, C, D\}$ in the spectral domain for the different regions in FIG. 3B. The auto-correlation is computed using the following equation:

$$r[\tau] = \sum_{n=0}^{N-1} S[n]S[n-\tau], \quad -\frac{1}{2}N < \tau < \frac{1}{2}N \quad (12)$$

The frequency corresponding to the largest peak in the spectrum is denoted as F and is considered the HR frequency in regions that contain skin. This feature can be derived as follows:

$$F = \hat{k} \cdot \frac{f_s}{N} \quad (13)$$

where $f_s$ is the sample frequency and $f_s/N$ is the resolution in the spectral domain. Index $\hat{k}$ of the frequency bin corresponding to the largest peak is located as follows:

$$\hat{k} = \arg\max_k \{\hat{R}[k] \mid k \in [0, (N-1)/2]\} \quad (14)$$

The phase angle θ of the pulse signal can be derived as follows:

$$\theta = \arctan\left(\frac{\text{Im}(S[\hat{k}])}{\text{Re}(S[\hat{k}])}\right) \quad (15)$$

where $\theta \in [-\pi, \pi]$.

Figure 8A:
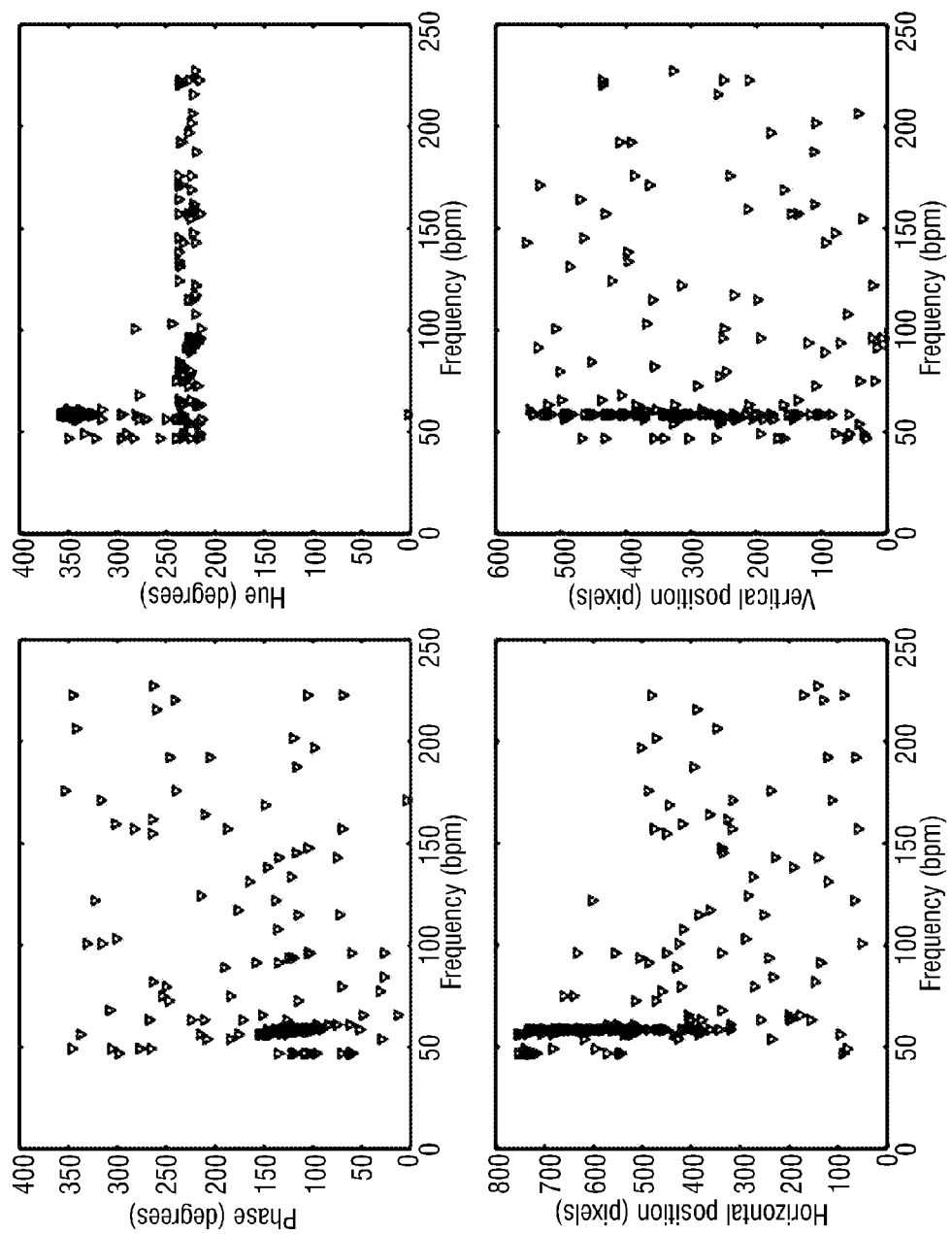
FIG. 8A shows scatter plots of the feature space from all regions.

The region can be represented as a point $p=[F, \theta, H, P_g]$ in a multidimensional feature space. FIG. 8A shows scatter plots of the feature space for the regions from the example video sequence where $P_g$ is separated in the horizontal and vertical position. In these scatter plots it can be seen that there is a dense area of points corresponding to the skin regions.

To reduce the amount of regions which are forwarded to the clustering, a prefiltering stage is preferably applied where regions with certain characteristics are readily identified as background. Therefore, several conditions may be used for regions which are necessary in order to be selected for the clustering.

Figure 4A:
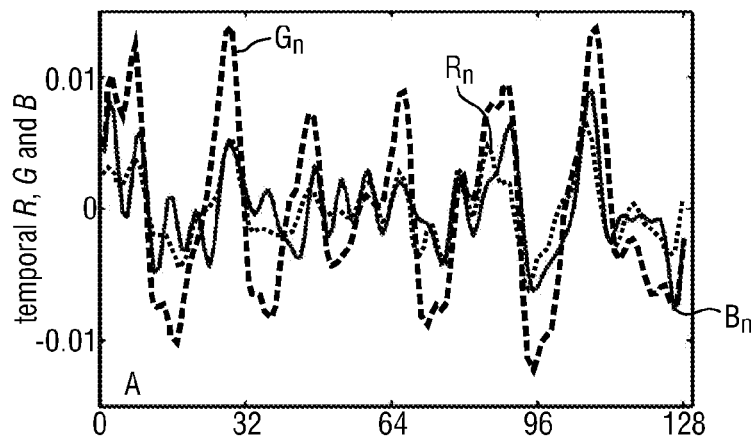
FIG. 4A shows a diagram of normalized color channels related to region A of FIG. 3B.
Figure 4B:
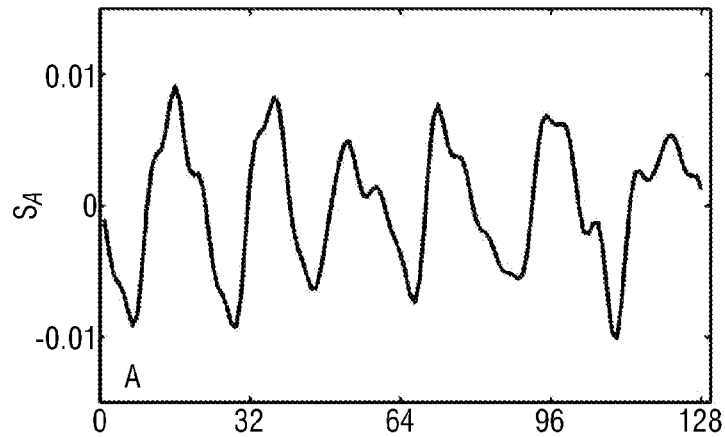
FIG. 4B shows a diagram of pulse signals corresponding to region A of FIG. 3B.
Figure 4C:
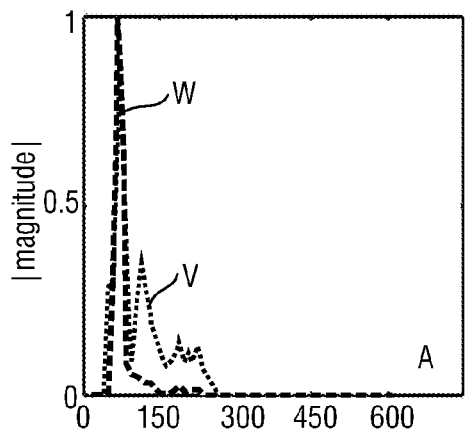
FIG. 4C shows a diagram of normalized spectra of pulse signals and of auto-correlation of pulse signals corresponding to region A of FIG. 3B.
Figure 5A:
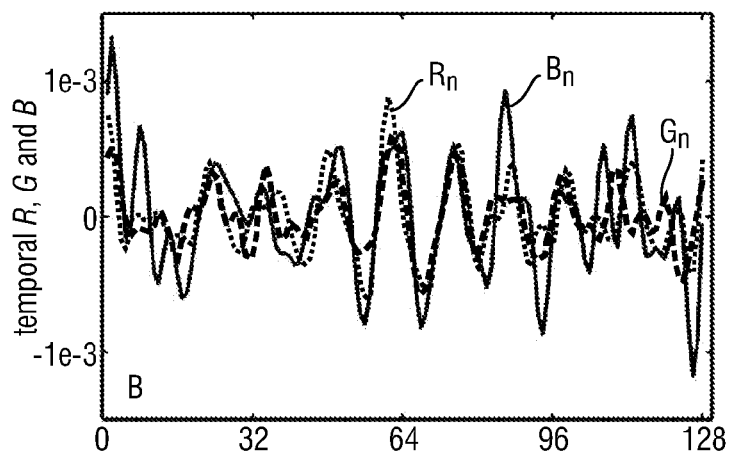
FIG. 5A shows a diagram of normalized color channels related to region B of FIG. 3B.
Figure 5B:
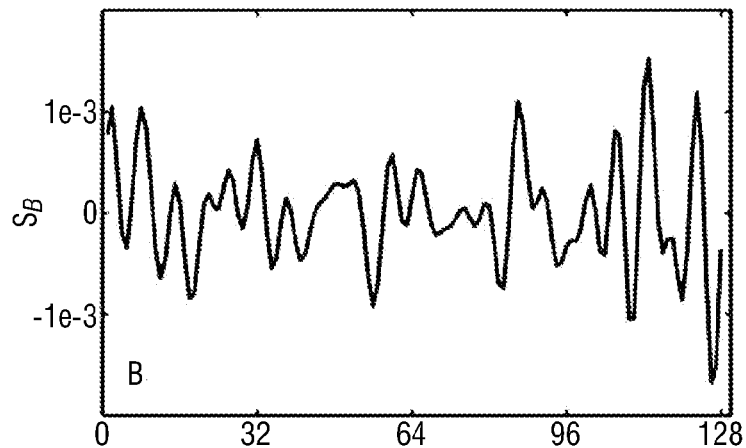
FIG. 5B shows a diagram of pulse signals corresponding to region B of FIG. 3B.
Figure 5C:
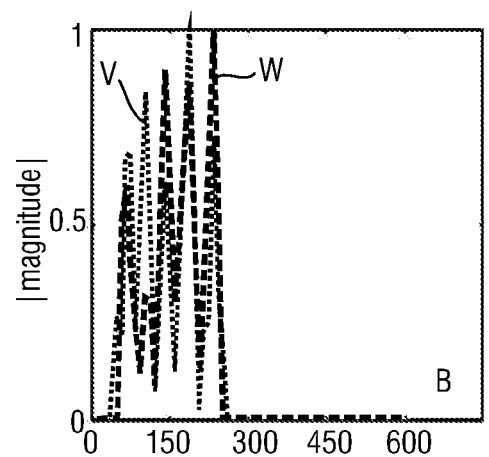
FIG. 5C shows a diagram of normalized spectra of pulse signals and of auto-correlation of pulse signals corresponding to region B of FIG. 3B.
Figure 6A:
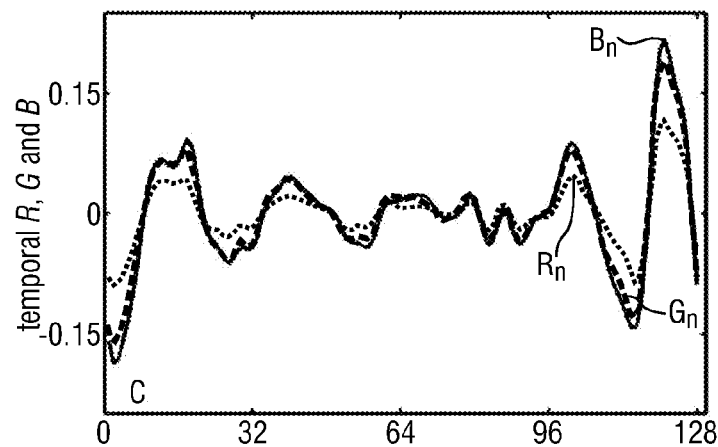
FIG. 6A shows a diagram of normalized color channels related to region C of FIG. 3B.
Figure 6B:
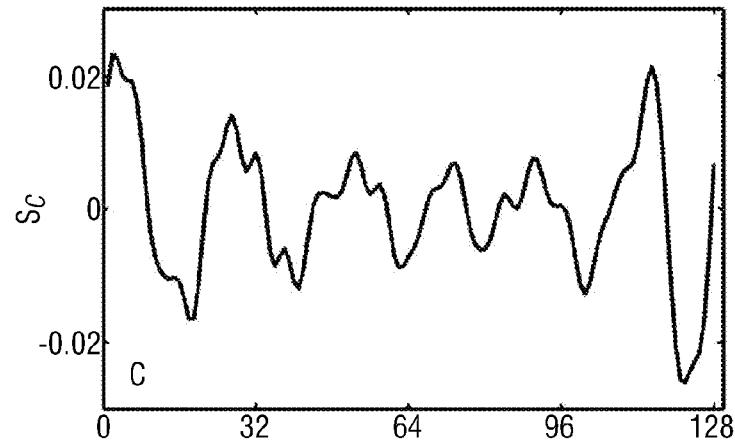
FIG. 6B shows a diagram of pulse signals corresponding to region C of FIG. 3B.
Figure 6C:
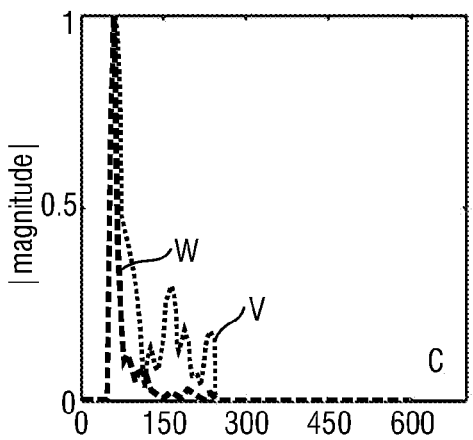
FIG. 6C shows a diagram of normalized spectra of pulse signals and of auto-correlation of pulse signals corresponding to region C of FIG. 3B.
Figure 7A:
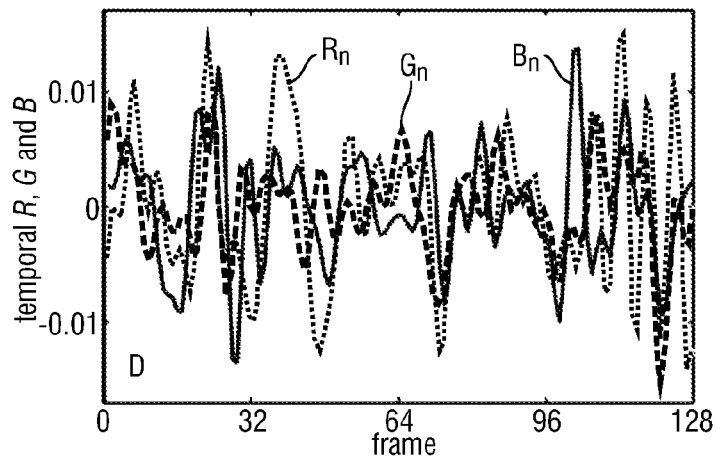
FIG. 7A shows a diagram of normalized color channels related to region D of FIG. 3B.
Figure 7B:
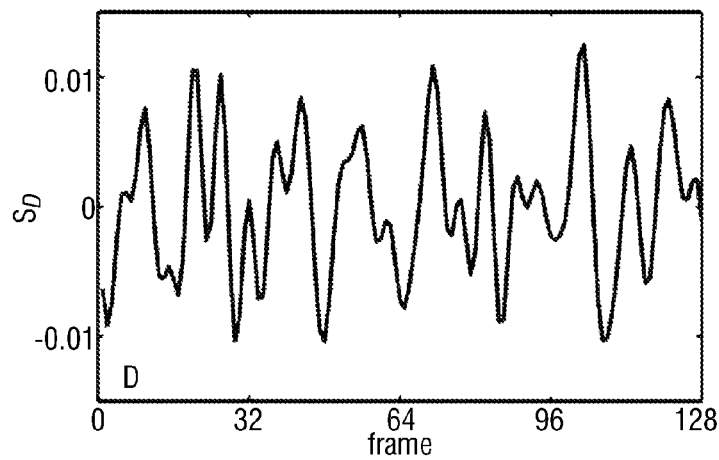
FIG. 7B shows a diagram of pulse signals corresponding to region D of FIG. 3B.
Figure 7C:
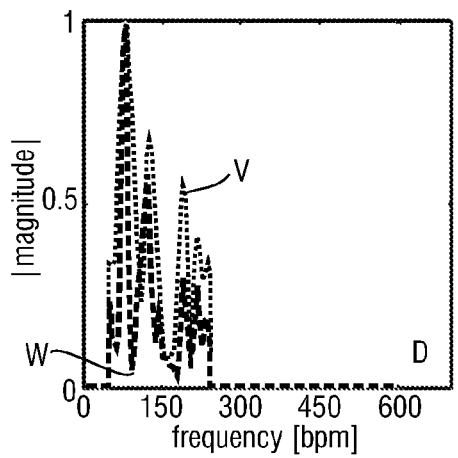
FIG. 7C shows a diagram of normalized spectra of pulse signals and of auto-correlation of pulse signals corresponding to region D of FIG. 3B.

As a first condition color traces may be used. In the above, it has been assumed that the region content is fixed due to the application of region tracking. However, regions containing object boundaries can still be subject to changes in content due to movement. An example of such regions is indicated with "C" in FIG. 3B. The amplitudes of the resulting normalized color traces are significantly larger than the color changes caused by blood pulsation as can be seen in FIG. 4A. On the other hand, the color changes in regions containing only background are due to noise and exhibit small amplitudes. An example of a background region is shown in FIG. 3B indicated with "B" and the resulting color changes can be seen in FIG. 4A. The peak amplitude for the normalized color traces $C \in \{R_n, G_n, B_n\}$ is computed using:

$$\delta_{C,max} = \max\{C[n] \mid n \in [0, N-1]\} \quad (16)$$

where N is the interval length. The regions containing peak amplitudes that are outside the range [0.005, 0.15] are identified as background. Furthermore, skin regions exhibit different amplitudes while remaining in-phase due to the different blood absorption rates of individual color channels. In order to assess the amplitude differences between the color traces, the normalized Sum of Absolute Differences (SAD) is computed using the following equation:

$$\delta_{SAD} = \frac{\sum_n |x[n] - y[n]|}{\sum_i |x[n]|} \quad (17)$$

and regions outside the range $\delta_{SAD} \in [0.05, 0.5]$ are identified as background. To find phase similarities of the color traces, the Normalized Correlation Coefficient (NCC) between the color traces is computed using the following equation:

$$\delta_{NCC} = \frac{\sum_n x[n] \cdot y[n]}{\sqrt{\sum_n x[n]^2 \cdot \sum_n y[n]^2}} \quad (18)$$

The regions containing peak amplitudes that are outside the range $\delta_{NCC} \in [0.5, 0.99]$ are identified as background.

Figure 8B:
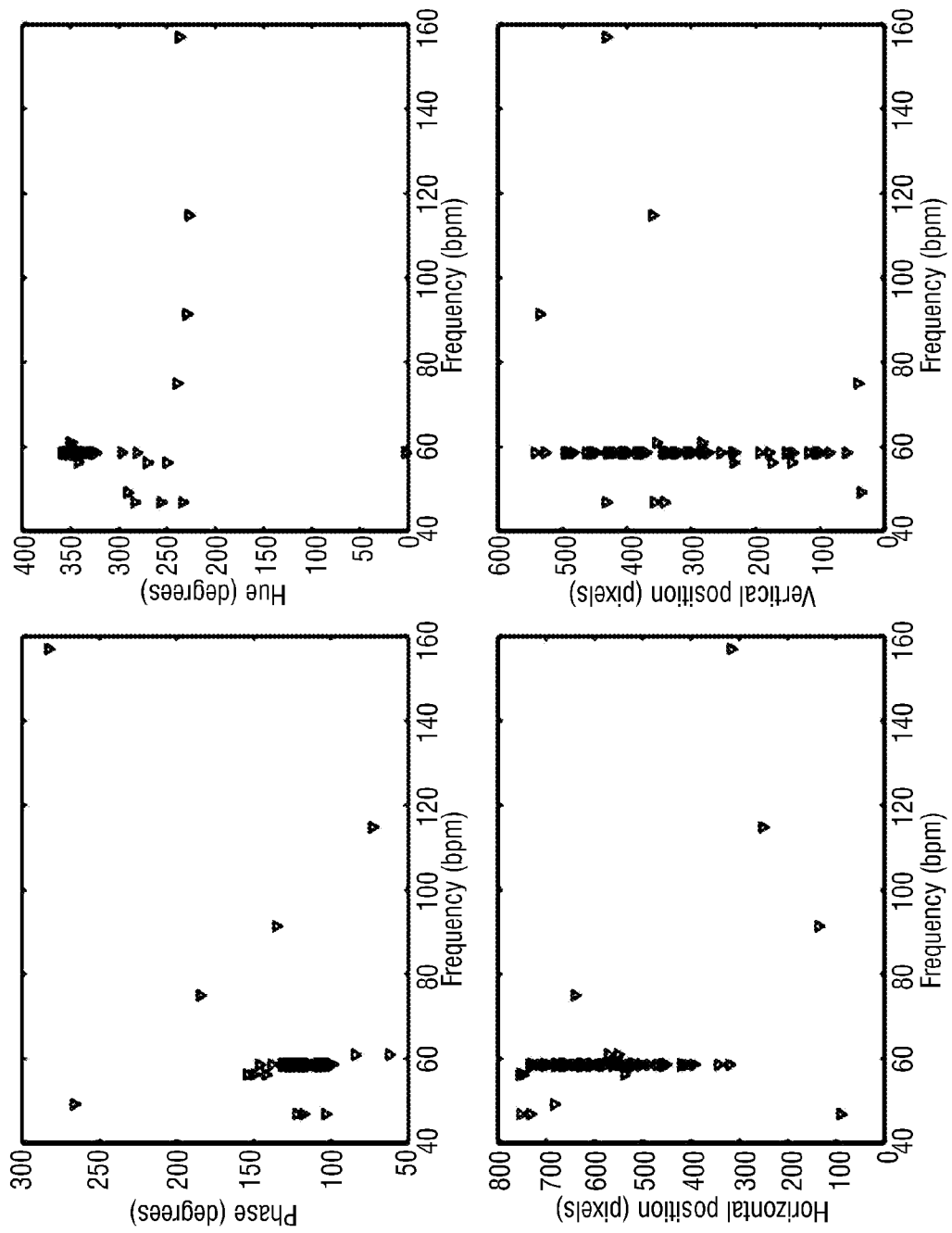
FIG. 8B shows scatter plots of the feature space from regions passing a prefiltering stage in clustering.

As a first condition pulse signal may be used. To determine the presence of a dominant frequency, the ratio between the two largest peaks in the spectrum is calculated as:

$$PR = \frac{P_{max2}}{P_{max1}} \quad (19)$$

for which $0 \leq PR \leq 1$ where the upper-bound corresponds to the case that the amplitude of the peaks are identical and the lower bound corresponds to the case there is exactly one frequency present. The regions where $PR > 0.6$ are identified as background. Furthermore, the peak amplitude of the pulse signal is computed as follows:

$$\delta_{S,max} = \max\{S[n] \mid n \in [0, N-1]\} \quad (20)$$

and the regions where $\delta_{S,max} < 0.005$ are identified as background. The parameters discussed here are chosen empirically. In FIG. 8B, the feature space of the example video sequence is shown where only the regions selected for clustering are shown. As can be seen, the dense area of points is still present whereas a greater part of the background regions are removed.

Figures 9A, 9B:
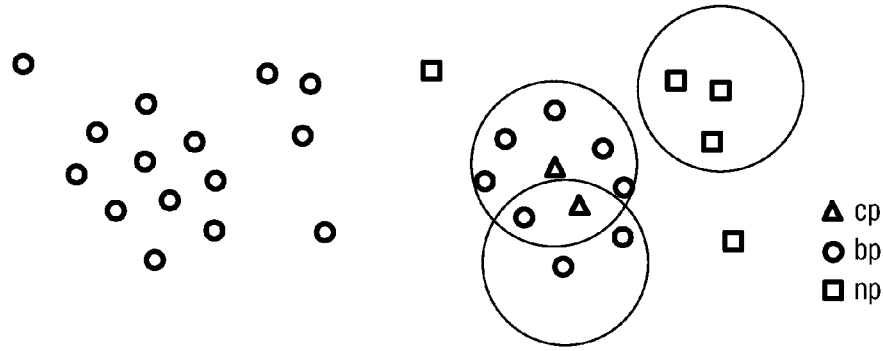
FIG. 9A shows an example of a distribution of points in a 2-dimensional space within the radius of a circle.
FIG. 9B shows an example of the partitioning of a distribution of points in a 2-dimensional space using a given range and minPts.

After eliminating the regions which can readily be identified as background, the remaining regions are grouped based on their features. In the scatter plots of the feature space for the example video sequence, an area of points can be clearly recognized for which the density is considerably higher than outside the area. These points in the feature space correspond to regions in the interval which contain skin. The points located outside the dense area correspond to background regions and are considered noise. A clustering method which relies on a density-based notion of clusters is the Density-Based Spatial Clustering of Applications with Noise (DBSCAN) method as described in M. Ester, H. Kriegel, J. Sander, and X. Xu, "A density-based algorithm for discovering clusters in large spatial databases with noise", KDD, 1996. This method separates points into three different types using a density threshold with two parameters, $\epsilon$ specifying a range and minPts denoting a minimal number of points. A point is called a cluster core point if it has at least minPts points within the range $\epsilon$. The points lacking this requirement yet having a core point within the range belong to that cluster and are called border points. The remaining points do not belong to any cluster and are called noise points. FIG. 9A shows an example of the partitioning of a distribution of points in a 2-dimensional space where E is the radius of a circle. FIG. 9B shows the results of partitioning the points with $\epsilon=1$ and minPts=6. The core points cp have a minimum of 6 neighboring points within a radius of 1 (circle). The border points by have maximally 5 neighboring points np including a core point cp within a radius of 1 (circle). The remaining points are noise points np.

Figure 10B:
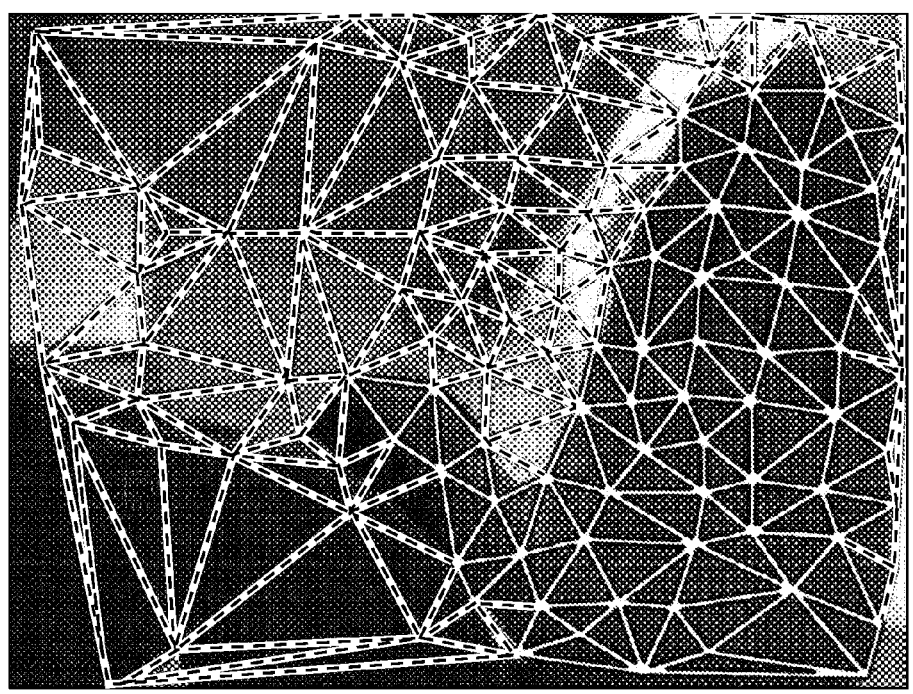
FIG. 10B shows the result of automatic skin detection for an example video sequence.
Figure 10A:
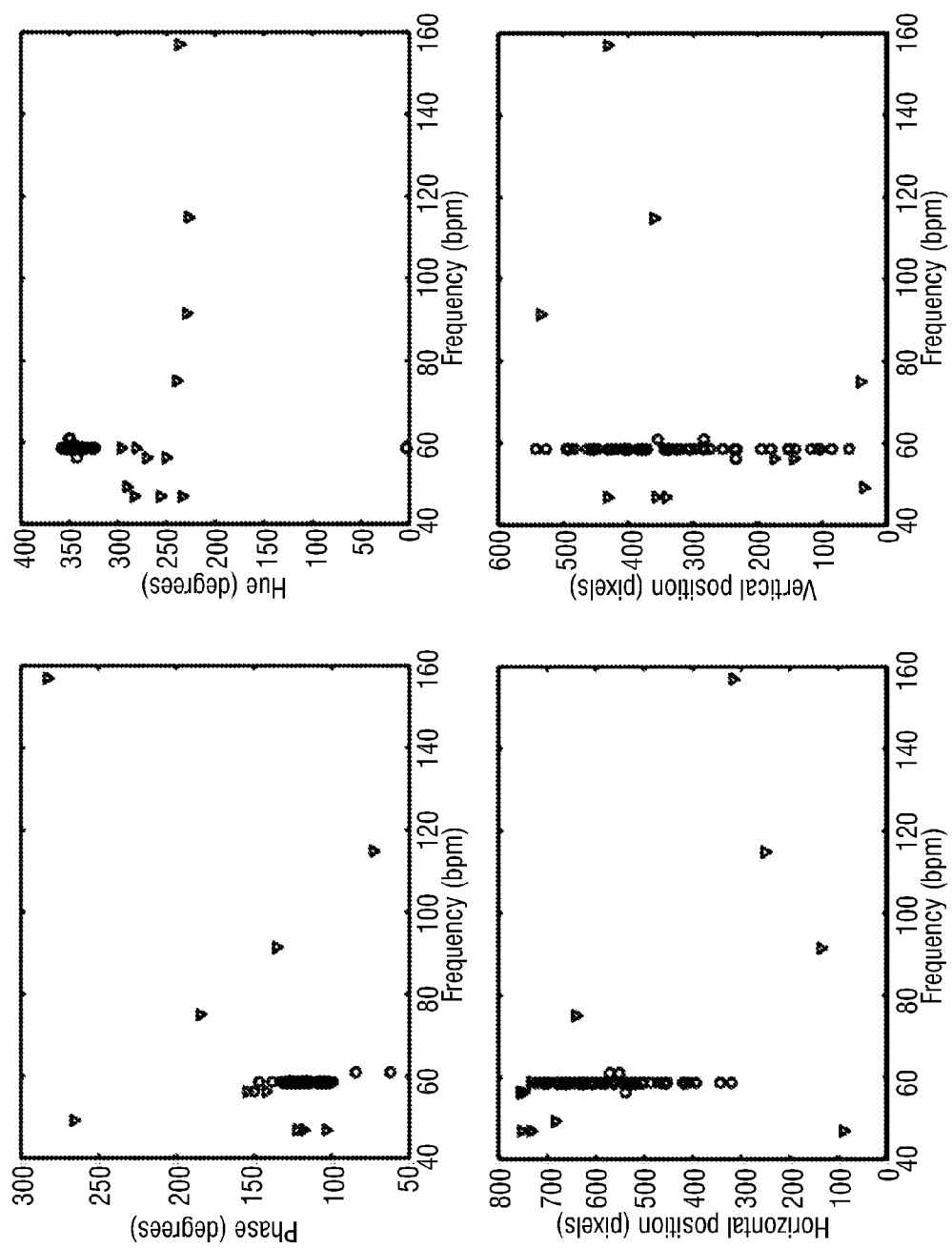
FIG. 10A shows scatter plots of feature space of regions that pass a prefiltering step.

This density-based approach to clustering can be increased to any higher dimensional space. Furthermore, the range can be shaped arbitrary by using a separate distance parameter for every feature in the space. To determine whether regions are located within in the range of each other is computed as follows:

$$N_{i,j} = \begin{cases} \text{true} & |p_i - p_j| \leq \varepsilon \\ \text{false} & \text{elsewhere} \end{cases} \quad (21)$$

where the range $\epsilon=[3, 10, 10, 100]$ is empirically determined. The minimum number of points in a cluster is defined as minPts=6. FIG. 10 shows the clustering results for the example video sequence using these parameters. FIG. 10A shows scatter plots of the feature space of regions that pass the prefiltering step. The points indicated by circles belong to the skin regions. FIG. 10B shows clustering results for example video sequence. It can be seen that the most skin regions are determined correctly.

It is possible that some regions containing skin are falsely identified as background regions as a consequence of the preprocessing. These regions lack the conditions necessary for clustering but still may contain strong pulse signals. In order to retrieve these particular skin regions, a cluster growing is performed. For this growing procedure, the average pulse signal of a cluster is compared to the pulse signal of surrounding regions using (18). When the pulse signal of a region corresponds significantly ($\gamma_{NCC}>0.5$) to the pulse signal of the cluster, the region is added to the cluster. Since the pulse signals of the regions in the clusters are likely to have different amplitudes, the pulse signals are normalized using:

$$Sn_r = \frac{S_r}{\sigma(S_r)} \quad (22)$$

where $\sigma(S_r)$ is the standard deviation of $S_r$. To minimize the effects of outliers caused by noise we combine the pulse signals of the regions using the alpha-trimmed mean. The average pulse signal of the cluster is obtained by eliminating the highest and the lowest values of each time period and averaging over the remaining values, i.e. for every sample $i \in \{1 \ldots 128\}$ and for all regions $r \in \{1 \ldots M\}$ within the cluster, the data $Sn_{r,i}$ is ordered in such a way that $\forall_i \forall_{r \in (1 \ldots M-1)}$ holds that $Sn_{r,i} \leq Sn_{r+1,i}$. The average pulse signal of the cluster is then obtained as follows:

$$S_{c,i} = \frac{1}{(1-\alpha)M} \sum_r Sn_{r,i} \quad (23)$$

where $$\left(\frac{\alpha}{2}M + 1\right) \leq r \leq \left(1 - \frac{\alpha}{2}\right)M$$

and $0 \leq \alpha \leq 1$ where $\alpha$ is set to 0.5.

To further increase the robustness of the proposed method, i.e. ensuring the ROI is properly detected throughout the video sequences, the resulting pulse signal for the complete video sequence is compared to a reference signal. The pulse signal throughout the complete video sequence can be obtained by repeating the detection of the ROI and concatenating the resulting pulse signals. To prevent discontinuity at the edges of intervals, the ROI estimation is performed in an overlapping fashion and the resulting pulse signals are stitched together using Hann windowing on individual intervals:

$$S_i = \sum_N wh_{N,i} S_{N,i} \quad (24)$$

where $S_{N,i}$ is the pulse signal in image i obtained from the Nth ROI estimator and $wh_{N,i}$ is the Hann windowing function centered in interval N and zero outside the interval:

$$wh_{N,i} = 0.5 - 0.5 \cos(2\pi i/\text{interval}) \quad (25)$$

Figure 11:
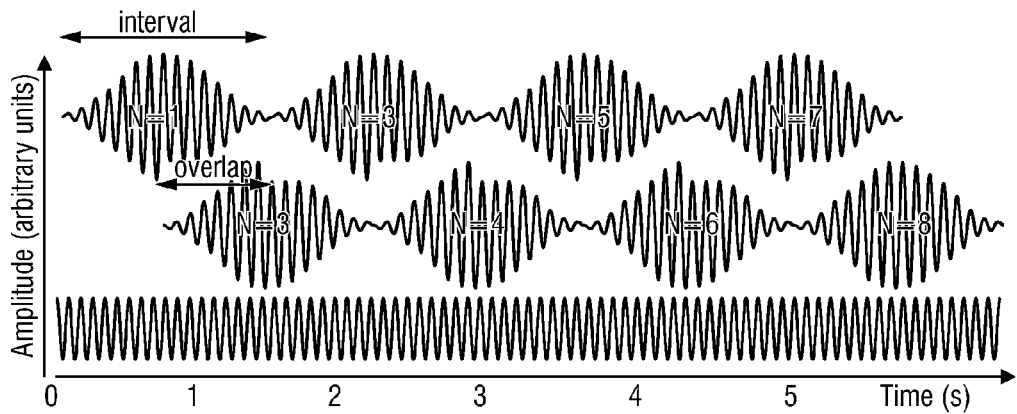
FIG. 11 shows an illustration of the overlap-add procedure.

An illustration of the overlap-add procedure is shown in FIG. 11. In interval where the ROI could not be determined, the interval pulse signal is replaced with a signal consisting of zeros to ensure continuity of the output pulse signal. Furthermore, in the case that multiple clusters are found, the cluster containing the most regions is considered as ROI.

Figure 12:
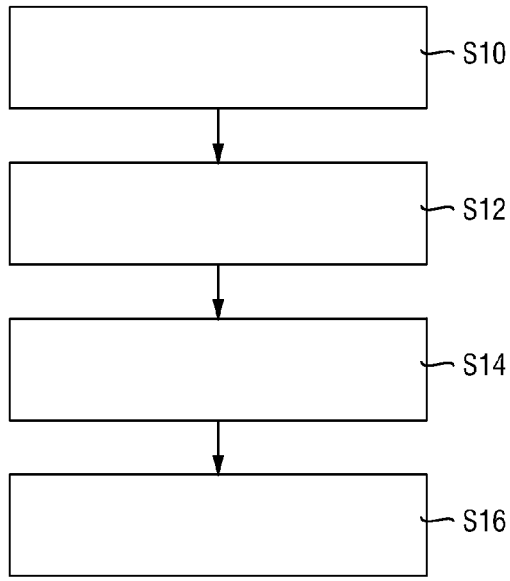
FIG. 12 shows a flow chart of an embodiment of a method according to the present invention.

FIG. 12 shows a flow chart of an embodiment of a method according to the present invention. In a first step S10 a sequence of image frames acquired over time is obtained. In a second step S12 an image frame of said sequence of image frames is segmented. In a third step S14 segments of the segmented image frame over time are tracked in said sequence of image frames. In a fourth step S16 the tracked segments are clustered to obtain clusters representing skin of a subject by use of one or more image features of said tracked segments.

The proposed device, system and method can be used for continuous unobtrusive monitoring of PPG related vital signs (e.g. heartbeat, SpO2, respiration), and can be used in NICU, Operation Room, or General Ward. The proposed device, system and method can be also used for personal health monitoring. Generally, the present invention can be used in all applications where skin needs to be detected in an image of a scene and needs particularly to be distinguished from non-skin, e.g. in surveillance applications such as access control or safety monitoring.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for skin detection of vital sign information, comprising:
   a color video camera configured to acquire a sequence of color image frames;
   a control computer processor configured to:
      receive the sequence of image frames,
      segment the images frames of said sequence of image frames,
      track segments of the segmented image frames in said sequence of image frames,
      cluster the tracked segments using temporal color variations of the tracked segments as a feature for clustering the tracked segments to obtain clusters representing skin of a subject, and
      extract vital sign information from the clustered tracked segments; and
   a user interface including a display configured to be controlled by control computer processor to display the extracted vital sign information.

2. The system as claimed in claim 1, wherein the control processor is further configured to perform a Fourier transformation of a spatially combined color value of at least part of the pixels in the tracked segments and to cluster two tracked segments into a single cluster if their amplitude peak frequency has substantially the same value and phase.

3. A device for skin detection comprising:
   an input unit for obtaining a sequence of image frames acquired over time,
   a segmentation unit for segmenting an image frame of said sequence of image frames,
   a tracking unit for tracking segments of the segmented image frame over time in said sequence of image frames,
   a clustering unit for clustering the tracked segments to obtain clusters representing skin of a subject by use of one or more image features of said tracked segments,
   wherein said clustering unit is configured to compute the inner product between normalized time signals of different tracked segments and to cluster said tracked segments into a single cluster if said inner product exceeds a predetermined threshold.

4. The device as claimed in claim 3, wherein said segmentation unit is configured to over-segment the image frame that is used for segmentation.

5. The device as claimed in claim 3, wherein said clustering unit is further configured to use the hue of pixels of the tracked segments as feature for clustering the tracked segments.

6. The device as claimed in claim 3, wherein said segmentation unit is configured to perform a Harris corner detection.

7. The device as claimed in claim 3, wherein said segmentation unit is configured to perform a Delaunay triangulation.

8. A system for skin detection comprising:
   a video camera configured to acquire the sequence of image frames over time; and
   the device for skin detection as claimed in claim 3 based on the acquired sequence of image frames.

9. A device for skin detection comprising:
   a camera configured to acquire a sequence of image frames of skin of a subject over time;
   a user interface including a display; and
   a computer programmed to:
      segment the image frames of said sequence of image frames,
      track segments of the segmented image frames of the sequence of image frames over time,
      cluster the tracked segments to obtain clusters representing skin of a subject using one or more image features of the tracked segments,
      repeatedly perform the segmentation, the tracking and the clustering, wherein the sequence of acquired image frames used for subsequent repetitions overlap in time,
      repeatedly extract physiological information from the clustered tracked segments, and
      controlling the user interface display to display the extracted physiological information.

10. The device as claimed in claim 9, wherein the computer is programmed to over-segment the image frames based on color, position and/or texture properties.

11. The device as claimed in claim 9, wherein the computer is programmed to track the segments of the segmented image frames using motion estimation.

12. The device as claimed in claim 9, wherein the physiological information includes vital signs of the subject.

13. A method for skin detection comprising:
   obtaining a sequence of image frames of a subject acquired over time,
   segmenting the image frames of said sequence of image frames to define segments,
   tracking the segments of the segmented image frames over time in said sequence of image frames,
   clustering the tracked segments to obtain clusters representing skin properties of the subject by use of one or more image features of said tracked segments, and
   iteratively repeating the segmenting, tracking, and clustering to update the skin properties, wherein the sequence of image frames of subsequent repetitions overlap in time.

14. A non-transitory computer-readable medium carrying program code for controlling a computer to carry out the steps of the method as claimed in claim 13.

15. The method as claimed in claim 13, further including:
   detecting vital signs of the subject in the updated skin properties, and
   controlling a user interface to display the vital signs.

16. The method as claimed in claim 13, wherein the sequence of video frames is acquired with a color video camera and the clustering is based on temporal color variations of the tracked segments.

17. The method as claimed in claim 13, further including:
   computing an inner product between normalized time signals of different tracked segments, the tracked segments being clustered into a single cluster if the inner product exceeds a predetermined threshold.

* * * * *